Dec. 30, 1958 H. C. SWIM Plant Pat. 1,786
ROSE PLANT
Filed Jan. 7, 1958
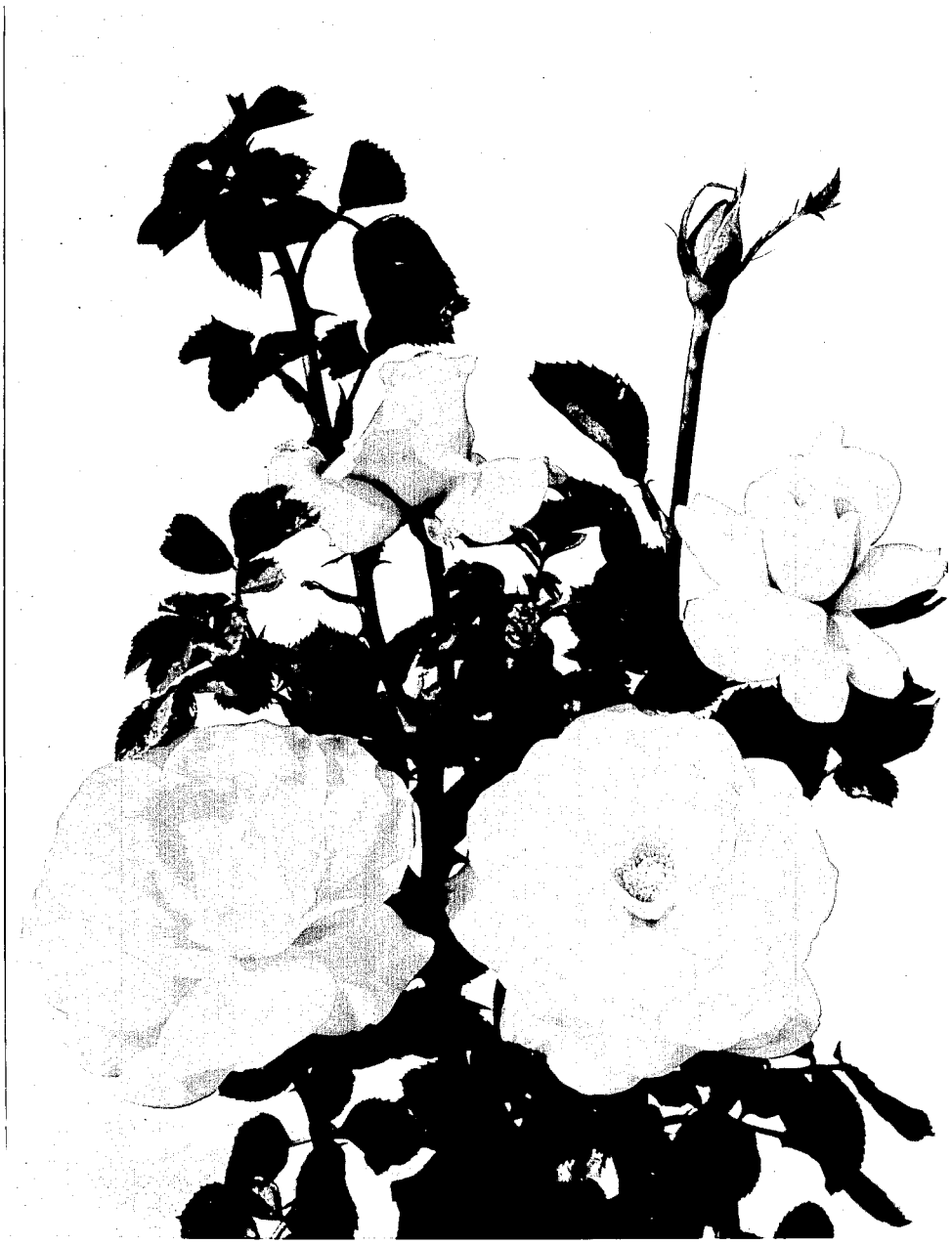
Inventor.
H. C. Swim
By: Robb & Robb
Attorneys.

United States Patent Office

Plant Pat. 1,786
Patented Dec. 30, 1958

1,786

ROSE PLANT

Herbert C. Swim, Ontario, Calif., assignor to Armstrong Nurseries, Inc., Ontario, Calif., a corporation of California Application January 7, 1958, Serial No. 707,656

1 Claim. (Cl. 47—61)

The present invention relates to a new and distinct variety of rose plant of the floribunda class, which was originated by me by crossing an unnamed and unpatented variety with the variety "Roundelay" (Plant Patent No. 1,280), the latter being the pollen parent, and the former being the seed parent.

The unnamed seed parent was a rose of the floribunda type which had a vigorous and upright habit of growth, and bore flowers in clusters, with each flower having a double form, averaging from 3½ to 4 inches in diameter, and being of a scarlet-orange color.

The primary objective of this breeding was to produce a new and improved variety of rose plant which combines the most desirable characteristics of the parent varieties. This objective was fully achieved, as evidenced by the following characteristics which are outstanding in the new variety, and which definitely differentiate the same from its parents, as well as from all other varieties of which I am aware:

(1) The large, bushy, vigorous and floriferous habits of plant growth;

(2) The habit of bearing flowers both singly and in small clusters;

(3) Relatively long individual flower stems which are considerably longer than those of the average floribunda rose, making the new variety desirable and suitable for cut flowers;

(4) A very attractive and nearly perfect urn-shaped bud form;

(5) Double flowers ranging from medium to large in size;

(6) Better than average petal substance, with attendant long-lasting quality of the flowers; and (7) A bright and relatively unfading scarlet-orange general color tonality of the flowers, somewhat resembling that of the variety "Aztec" (Plant Patent No. 1,648), but more red than the latter.

In comparison with its seed parent, the form of the buds of my new variety is more nearly a perfect urn shape than that of this parent, its flowers are borne in somewhat smaller clusters, as well as on some single stems which rarely occurs in the case of the seed parent, and the color of the flowers is slightly darker and somewhat more red than that of this parent.

As compared with its pollen parent, "Roundelay," the plant of the new variety is somewhat less vigorous in its habit of growth, the flowers are borne in larger clusters, but the stems are relatively shorter on the average than those of this parent, the flowers have fewer petals, and the flower color is scarlet-orange instead of dark red like the flower color of this parent.

Asexual reproduction of my new variety by budding, as performed at Ontario, California, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Robert F. Wilson's Horticultural Colour Chart (hereinafter abbreviated as "Wilson") and Robert Ridgway's Color Standards and Nomenclature (hereinafter abbreviated as "Ridgway"), as indicated:

Type: Bush; greenhouse and outdoor; seedling; for cut flowers and for garden decoration.

Class: Floribunda.

Breeding: Seedling.

*Seed parent.*—An unnamed seedling.

*Pollen parent.*—"Roundelay."

Propagation: Holds its distinguishing characteristics through succeeding propagations by budding.

*Flower*

Locality where grown and observed: Ontario, California.

Flowers borne: Sometimes singly, but usually 3 or 4 or more to the stem; in regular, rounded clusters; on strong stems of a length varying from medium to long.

Quantity of bloom: Abundant, both outdoors and in greenhouse.

Continuity: Continuous during growing season.

Fragrance: Slight.

Bud:

*Peduncle.*—Average length; average caliper; erect; smooth; with few gland-tipped cilia. Color—near Lime Green, Plate XXXI (Ridgway), overlaid with near Liver Brown, Plate XIV (Ridgway) on side exposed to sun.

*Before calyx breaks.*—Size—medium. Form—medium length; ovoid; with foliaceous appendages and some gland-tipped cilia on the surface of the bud; with slender, foliaceous parts extending beyond the tip of the bud equal to from ¼ to ½ of its length.

*As calyx breaks.*—Color—near Chrysanthemum Crimson, Plate 824, page 169 (Wilson).

*Sepals.*—Inner surface with fine, woolly tomentum; margins of alternate sepals lined with fine, woolly tomentum; others lined with gland-tipped cilia.

*As first petal opens.*—Size—average. Form—from short to medium length; urn-shaped. Color outside—between Current Red, Plate 821/2, page 167 (Wilson) and Cardinal Red, Plate 822/1, page 168 (Wilson), with small area at base of petal near attachment near Sap Green, Plate 62/2, page 62 (Wilson); inside—between Blood Red, Plate 820/1, page 166 (Wilson) and Cardinal Red, Plate 822, page 168 (Wilson), with small area at base of petal near attachment near Sap Green, Plate 62/2, page 62 (Wilson).

*Opening.*—Opens up well; is not retarded from opening by cold, hot, wet or dry weather.

Bloom:

*Size (when fully open).*—From average to large; from 3½ inches to 4½ inches.

*Petalage.*—Double; from 26 to 36 petals, plus from 5 to 8 petaloids; arranged regularly.

*Form.*—High-centered and somewhat globular at first, but becoming open to cupped; petals being at first somewhat loosely cupped but becoming later at maturity flat-cupped, with lateral margins of intermediate petals usually reflexed slightly, and with lateral margins of outer petals usually reflexed from ¼ to ⅓ of upper portion of petal.

Petals:

*Texture.*—Thick; leathery. Inside—velvety. Outside—from shiny to satiny.

*Shape.*—Outside—broadly obovate, with apex flat, and sometimes with one or two notches. Intermediate—obovate, with apex from rounded to flat. Inside—obovate; somewhat irregular; with apex rounded and sometimes with one or two notches.

This description of a newly opened flower was made from a rose grown outdoors in the month of November at Ontario, California:

*Color.*—Outer petal: outside surface—between Turkey Red, Plate 721/2, page 94 (Wilson) and Current Red, Plate 821/3, page 167 (Wilson), with small area at base of petal near attachment near Dresden Yellow, Plate 64/3, page 64 (Wilson); inside surface—between Turkey Red, Plate 721/2, page 94 (Wilson) and Current Red, Plate 821/3, page 167 (Wilson), with small area at base of petal near attachment near Dresden Yellow, Plate 64/3, page 64 (Wilson). Intermediate petal: outside surface—between Turkey Red, Plate 721/2, page 94 (Wilson) and Crimson, Plate 22, page 22 (Wilson), with small area at base of petal near attachment near Dresden Yellow, Plate 64/3, page 64 (Wilson); inside surface—between Turkey Red, Plate 721/1, page 94 (Wilson), and Carmine, Plate 21, page 21 (Wilson), with small area at base of petal near attachment near Dresden Yellow, Plate 64/3, page 64 (Wilson). Inner petal: outside surface—between Turkey Red, Plate 721/2, page 94 (Wilson) and Currant Red, Plate 821/3, page 167 (Wilson), with small area at base of petal near attachment near Dresden Yellow, Plate 64/3, page 64 (Wilson); inside surface—between Turkey Red, Plate 721, page 94 (Wilson) and Orient Red, Plate 819/2, page 165 (Wilson), with small area at base of petal near attachment near Dresden Yellow, Plate 64/3, page 64 (Wilson).

This description was made from a rose that was open for 3 days outdoors in the month of November at Ontario, California:

*Color.*—Outer petal: outside surface—between Turkey Red, Plate 721/3, page 94 (Wilson) and Cardinal Red, Plate 822/3, page 168 (Wilson), with small area at base of petal near attachment near Dresden Yellow, Plate 64/3, page 64 (Wilson); inside surface—near Turkey Red, Plate 721/2, page 94 (Wilson), with small area at base of petal near attachment near Dresden Yellow, Plate 64/3, page 64 (Wilson). Inner petal: outside surface—between Turkey Red, Plate 721/2, page 94 (Wilson) and Cardinal Red, Plate 822/3, page 168 (Wilson), with small area at base of petal near attachment near Dresden Yellow, Plate 64/3, page 64 (Wilson); inside surface—between Turkey Red, Plate 721, page 94 (Wilson) and Orient Red, Plate 819/3, page 165 (Wilson), with area at base near Dresden Yellow, Plate 64/3, page 64 (Wilson).

*General color effect.*—Newly opened flower—near Orient Red, Plate 819/2, page 165 (Wilson). 3-days open—between Turkey Red, Plate 721/1, page 94 (Wilson) and Orient Red, Plate 819/2, page 165 (Wilson).

*Behavior.*—Drop off cleanly; not particularly affected by cold, hot, wet or dry weather.

*Flower longevity.*—On bush in garden—4 or 5 days in November. Cut roses grown outdoors and kept at living-room temperatures—5 or 6 days in November.

*Reproductive organs*

Stamens: Average number; arranged regularly about pistils.

Filaments: From medium length to long; from 5 to 12 mm. in length; few without anthers. Color—near Neyron Rose, Plate 633, page 76 (Wilson).

Anthers: Medium size; all open approximately at once. Color: upper side—margins near Saffron Yellow, Plate 7/2, page 7 (Wilson), with remainder near Aureolin, Plate 3/3, page 3 (Wilson); under side—margins near Indian Yellow, Plate 6/2, page 6 (Wilson), with remainder near Auerolin, Plate 3/3, page 3 (Wilson).

Pollen: From moderate to abundant. Color—near Buttercup Yellow, Plate 5/2, page 5 (Wilson).

Pistils: Many; approximately 125 in number.

Styles: Moderately even; from short to average length; from 3 to 8 mm. in length; average caliper; bunched. Color—near Dresden Yellow, Plate 64/3, page 64 (Wilson).

Stigma: Color—near Sap Green, Plate 62/3, page 62 (Wilson).

Ovaries: Usually all enclosed in calyx, but some protruding from calyx.

Hips: Average length; globular; smooth; walls thick and fleshy. Color (¾ mature)—near Apricot, Plate 609, page 70, (Wilson) on side exposed to sun.

Sepals: Permanent; medium length; curled and recurved. Color: inside—near Lettuce Green, Plate V (Ridgway), sometimes overlaid somewhat with near Chocolate, Plate XXVIII (Ridgway); outside—near Biscay Green, Plate XVII (Ridgway), sometimes overlaid with near Chocolate, Plate XXVIII (Ridgway).

Seeds: Few; medium size; from 5 to 8 in number.

*Plant*

Foliage:

*Leaves.*—Compound of usually 3 to 5 leaflets; abundant; medium size; leathery; semi-glossy.

*Leaflets.*—Shape—ovoid, with apex acute; round base; margin simply serrate.

*Color.*—Mature: upper surface—near Dark Dull Yellow-Green, Plate XXXII (Ridgway); under surface—near Light Elm Green, Plate XVII (Ridgway). Young: upper surface—near Diamine Brown, Plate XIII (Ridgway); under surface—between Madder Brown, Plate XIII (Ridgway) and Prussian Red, Plate XXVII (Ridgway).

*Rachis (the supporting stem of the compound leaf).*—Average size. Upper side—grooved; with some stipitate glands on edges. Under side—moderately smooth.

*Stipules.*—From short to medium length; from narrow to medium width; with moderately short points turning out at an angle of less than 45°.

*Disease resistance.*—Mildly subject to mildew under late fall conditions as compared with other varieties grown under comparable cultural conditions at Ontario, California.

Growth:

*Habit.*—Bushy; upright; much-branched.

*Growth.*—Vigorous.

*Canes.*—From medium caliper to heavy.

*Main stems.*—Color—between Light Elm Green, Plate XVII (Ridgway) and Chromium Green, Plate XXXII (Ridgway). Large prickles—several; medium length; almost straight; with medium length, moderately narrow base; color—near Russet, Plate XV (Ridgway). Small prickles—very few; color—Tawny, Plate XV (Ridgway).

Hairs—none.

*Branches.*—Color—between Bice Green, Plate XVII (Ridgway) and Chromium Green, Plate XXXII (Ridgway). Large prickles—several; medium length; almost straight; with medium length, moderately narrow base; color—near Courge Green, Plate XVII (Ridgway). Small prickles—very few; color—near Lime Green, Plate XXXI (Ridgway). Hairs—none.

*New shoots.*—Color—near Prussian Red, Plate XXVII (Ridgway). Large prickles — several; medium length; almost straight; with medium length, moderately narrow base; color—near Madder Brown, Plate XIII (Ridgway). Small prickles—none. Hairs—none.

I claim:

A new and distinct variety of rose plant of the floribunda class, substantially as herein shown and described, characterized particularly as to novelty by its large, bushy, vigorous and floriferous habits of growth, its habit of bearing flowers both singly and in clusters, its relatively long individual flower stems which are suitable for cut flowers, the nearly perfect urn-shaped form of its buds, its double flowers of from medium to large size, its better than average petal substance and attendant long-lasting flower quality, the bright scarlet-orange general color tonality of its flowers, and the good retention of the flower color.

No references cited.